United States Patent
Conquorgood et al.

(10) Patent No.: US 7,514,041 B2
(45) Date of Patent: Apr. 7, 2009

(54) METHOD AND APPARATUS FOR TESTING HEAVY OIL PRODUCTION PROCESSES

(75) Inventors: Steve Conquorgood, Calgary, CA (US); Lowy Gunnewiek, Burlington, CA (US); Bob Reid, Don Mills, CA (US); Emil Nenniger, Oakville, CA (US); John Nenniger, Calgary, CA (US)

(73) Assignee: N-SOLV Corporation, Calgary, Alberta (CA)

( * ) Notice: Subject to any disclaimer, the term of this patent is extended or adjusted under 35 U.S.C. 154(b) by 821 days.

(21) Appl. No.: 10/900,476

(22) Filed: Jul. 28, 2004

(65) Prior Publication Data

US 2006/0024840 A1   Feb. 2, 2006

(51) Int. Cl.
*G01N 25/48* (2006.01)
*G01N 33/26* (2006.01)
*G01N 1/18* (2006.01)

(52) U.S. Cl. ............ 422/82.12; 422/102; 422/104; 436/60; 436/147; 436/157; 436/178

(58) Field of Classification Search ............ 436/60, 436/147, 157, 178; 422/68.1, 82.12, 102, 422/104
See application file for complete search history.

(56) References Cited

U.S. PATENT DOCUMENTS

| | | | |
|---|---|---|---|
| 3,607,134 A * | 9/1971 | McIntyre | 422/104 |
| 4,335,620 A * | 6/1982 | Adams | 73/863.11 |
| 5,224,536 A * | 7/1993 | Eigen et al. | 165/290 |
| 5,446,263 A * | 8/1995 | Eigen et al. | 219/521 |
| 5,795,784 A * | 8/1998 | Arnquist et al. | 436/50 |
| 6,296,809 B1 * | 10/2001 | Richards et al. | 422/64 |
| 2003/0041663 A1 * | 3/2003 | Kossuth et al. | 73/159 |

* cited by examiner

*Primary Examiner*—Maureen M Wallenhorst
(74) *Attorney, Agent, or Firm*—Vidas, Arrett & Steinkraus, P.A.

(57) ABSTRACT

There is disclosed a method of testing oil extraction processes including the steps of: 1) placing a sample to be tested in a sample holder which has a configurable temperature profile; 2) placing the sample holder in a pressure vessel; 3) increasing the pressure in the pressure vessel to simulate an over burden pressure; 4) configuring the temperature profile of the sample holder to match a desired temperature profile; 5) applying an oil extraction process to the sample; 6) measuring one or more parameters of the oil extraction process; 7) measuring the temperature of the sample to which the process is being applied; and 8) configuring the sample holder to match the measured temperature profile. A device to test oil extraction processes on samples is also disclosed. The device has a temperature configurable sample holder having sufficient temperature control to provide a desired heat profile to the sample.

17 Claims, 8 Drawing Sheets

METHOD AND APPARATUS FOR TESTING HEAVY OIL PRODUCTION PROCESSES

FIELD OF THE INVENTION

This invention relates generally to the field of heavy oil or tar sand extraction, and more particularly to experimental techniques and methods that may be used to model temperature sensitive insitu extraction processes. Most particularly this invention relates to equipment and methods to model and test, on a small scale, insitu extraction processes for heavy oil and tar sands.

BACKGROUND OF THE INVENTION

This invention relates generally to the extraction of heavy oil and bitumen. Heavy oils are crude oils, which have high specific gravity and viscosity and are therefore difficult to extract commercially because they do not readily flow. Tar sands are geological formations in which heavy oil is trapped within a sand formation. Achieving insitu separation of the heavy oil from the sand is a well-known and difficult challenge.

Currently steam is the dominant thermal fluid used for insitu recovery of bitumen and heavy oil. Injected steam raises the temperature of the bitumen thereby reducing its viscosity and allowing it to flow more easily. Steam extraction is subject to a number of problems including high heat losses, clay swelling problems, thief zones, water-oil emulsions, capillary surface tension effects, lack of confinement for shallower zones and disposal of large quantities of environmentally damaging salt and organic acids as a consequence of boiler feed water purity requirements. By some estimates, with the best currently available technologies, only 10% of the original bitumen resource in the Athabasca tar sands are economic to extract.

Thermal recovery processes, using steam, also require large amounts of fuel to be burned to produce the steam and can emit enormous amounts of greenhouse gases such as carbon dioxide. Estimates published by Natural Resources Canada[1] show CO2 emissions of about 70 kg/bbl for bitumen production and a total of about 120 kg/bbl for synthetic crude (i.e. upgraded bitumen usually derived from surface mined bitumen).

[1] Canada's Emissions Outlook: an Update, December 1999, Annex B, pg B-6, Available at www.nrcan.gc.ca/es/ceo/update.htm Recent estimates released by the Alberta Energy Utilities Board[2] and the Canadian Association of Petroleum Producers[3], predict that bitumen (and synthetic crude) production rates will be 2 to 2.6 million bbl/day of bitumen by 2010. This level of bitumen production will produce at least 140 million kilograms (=70×2 million) of CO2 emissions per day (i.e. 300,000,000 to 700,000,000 lbs CO2 per day depending on fuel source and the proportion of insitu vs synthetic crude production).

[2] Alberta's Reserves 2000 and Supply/Demand outlook 2001-2010, Alberta Energy Utilities Board
[3] *Canada's Oil Sands Development* delivered by Eric Newell, Chairman & CEO, Syncrude Canada. Available at http://www.capp.ca/

Solvent extraction processes have been proposed as an alternative to steam extraction processes. One such process is the N-Solv process (Canadian Patent Applications, 2299790, 2351148, 2374115). However, the physical chemistry of the bitumen extraction in solvent gravity drainage processes is not very well understood or characterized. For example, Dunn[4] et al first reported in 1989, that for a cold solvent extraction process the measured CO2 diffusion rates in the tar sands were a factor of 460 times higher than the theoretically predicted values. This unexpected result has been observed and reported by many subsequent researchers using a variety of different solvents and crude oil samples and yet the underlying physical mechanism is still not understood.

[4] Dunn, Nenniger and Rajan, A Study of Bitumen Recovery by Gravity Drainage Using Low Temperature Soluble Gas Injection, Canadian Journal Of Chemical Engineering Vol 67, December 1989, pg 985

Several computer models have been developed to predict the extraction rates for gravity drainage bitumen extraction using solvent. However, these computer models do not appear to be capable of accurately describing the insitu processes. One potential problem of such models is a lack of spatial resolution because the models are typically far too coarse to accurately model the solvent concentration gradients. For example, lab studies by Fisher[5] have revealed that the solvent-bitumen interface is only a couple of millimeters thick. An appropriate gridblock size to accurately model insitu concentration gradients should be perhaps 10 times smaller (i.e. 100-200 microns). With typical grid block sizes of ~0.5 m used in computer modeled reservoir simulations (see Nghiem[6]), the calculated concentration gradients in the reservoir simulators are about 500 times smaller than values actually measured in the laboratory tests. For a 3D computer model with an appropriate spatial resolution the number of calculations increases by a factor of $5000^3$ (=125,000,000,000), which increases the model run time for a given scenario to an unworkable duration. Since the solvent concentration gradient provides the primary driving force for solvent penetration and extraction, existing computer models have a significant problem in accurately representing the process.

[5] Fisher et al, 'Use of Magnetic Resonance Imaging and Advanced Image Analysis as a Tool to Extract Information from a 2D Physical Model of the Vapex Process", Society of Petroleum Engineers Paper 59330, April, 2000
[6] Nghiem et al "Modelling Asphaltene Precipitation and Dispersive Mixing in the Vapex Process, SPE paper 66361, FIG. 2

As noted earlier, researchers consistently measure bitumen extraction rates with solvents that are much higher than expected. Thus, we believe, it is necessary to use physical models (i.e. experiments) to obtain meaningful data on bitumen yield, extraction rate and bitumen quality. Furthermore, until the details of the solvent extraction mechanism are better understood, we believe that it is unrealistic to expect credible predictions from the existing computer models.

Due to the complexity of physical processes (combined heat, mass and momentum transfer with simultaneous asphaltene precipitation) it may not be possible to ever develop a fully rigorous theoretical computer model. However, empirical models can be developed that are both accurate and useful. Such empirical models typically require data from a large number of representative physical experiments to be able to develop parametric sensitivities to process variables. This type of experimentation is expensive and time consuming, but has provided the basis for many (if not most) useful chemical engineering processes. However, it is necessary to conduct physical experiments which accurately represent the specific physical processes of interest and it is necessary that the same be accurately measured before a meaningful empirical model can be developed.

The prior art experimental apparatuses and techniques in the tar sand extraction field are generally intended to simulate a small two dimensional slice of a reservoir. These experiments are typically conducted in a thin walled rectangular can that is packed with tar sand (see Dunn[4] and Frauenfeld[7]) with physical properties relevant to the reservoir of interest. A simulated injector well is usually located above a simulated producer well at one end of the can. The can is placed within a pressure vessel and external pressure is applied to the can to mimic the overburden stresses appropriate to that reservoir.

[7] Frauenfeld et al., Evaluation of Partly miscible Processes for Alberta Heavy Oil Reservoirs, Journal of Canadian Petroleum Technology Vol 37 no 4, 1998

Tar sand extraction processes are typically based on some type of thermal effect and therefore appropriate consideration of thermal effects in the experiments is important. Two aspects of thermal behavior have been identified that can greatly affect the experimental modeling. First, there is a need to mimic to temperature profiles and temperature gradients within the tar sand which arise due to the thermal characteristics of the reservoir extraction process. Second, heat may be lost through the conductive nature of the can or sample holder of a typical experimental apparatus with the consequent distortion of the temperature profiles within the sandpack. Such heat loss is referred to as parasitic heat losses, Parasitic heat loss is an ongoing problem with all thermal gravity drainage experiments. Typically, SAGD researchers have used the dimensional scaling criteria of Butler, to work around this problem. Butler's scaling criteria predicts that by increasing the tar sand permeability, the time scale can be compressed (i.e. 1 hour of experimental time corresponds to 1 year of field time). Thus, scaled experiments minimize the impact of parasitic heat losses by greatly reducing the experimental time. Butler has used the analogy between heat transfer and mass transfer to develop similar scaling criteria for solvent processes[8]. However, as noted above, the solvent extraction mechanism is not well understood so the scaling assumptions of Butler's solvent model are in doubt. Thus a different approach from the prior art scaling assumptions of Butler is needed.

[8] Butler et al, A New Process (Vapex) for Recovering Heavy Oils by Using Hot Water and Hydrocarbon Vapour, Journal of Canadian Petroleum Engineering January-February 1991, vol 30, No. 1

Figure 1:
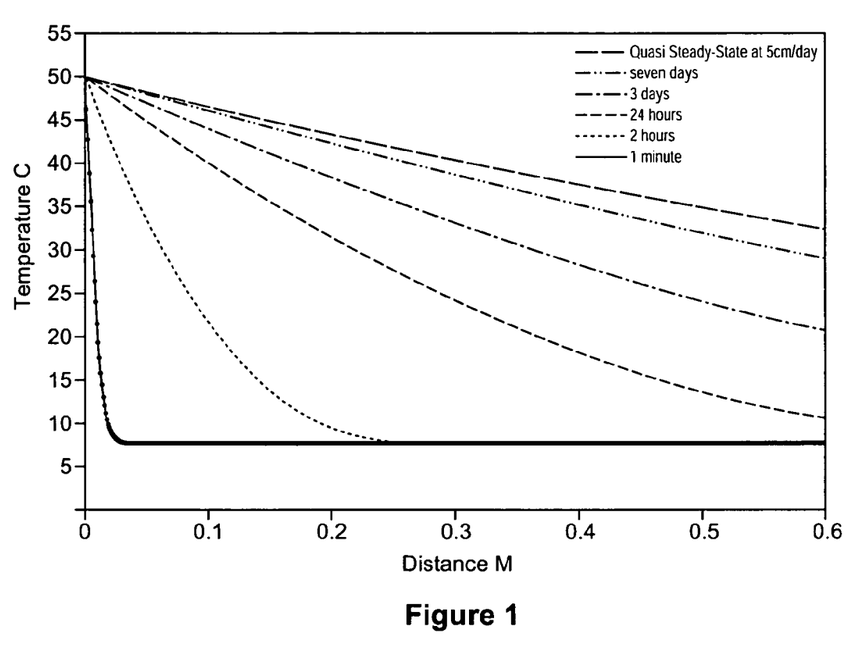
FIG. 1 shows the (one dimensional) temperature profiles along a 60 cm section of tar sand initially at 8 C after time intervals of 1 minute, 2 hours, one day, three days and ten days from when one edge is suddenly heated to 50 C.

FIG. 1 is based on prior art and illustrates the problem that the present invention seeks to address. FIG. 1 shows transient (one dimensional) temperature profiles at different times for a section of tar sand initially at 8C when one edge is suddenly heated to 50 C. In FIG. 1 zero on the x-axis represents a bitumen interface. FIG. 1 shows the temperature profiles along a 60 cm section of tar sand initially at 8 C after time intervals of 1 minute, 2 hours, one day, three days and seven days from when one edge is suddenly heated to 50 C. The physical properties of the tar sand and the temperature profiles were calculated using the data and formulas presented by Birrell[9]. FIG. 1 also shows a temperature profile expected for a continuous bitumen extraction process taking place in 8 C tar sand with the interface heated to 50 C and an assumed extraction rate of 5 cm/day again using the formulas presented by Birrell[9]. This latter temperature profile is referred to as a quasi-steady state profile, as it is not expected to change further over time (since the x-axis origin is the bitumen interface). FIG. 1 shows that it takes a period of seven days for a sample sandpack to acquire a smooth temperature profile (assuming no parasitic heat losses out the sides of the apparatus), but even then it does not have the same temperature profile predicted for "quasi-steady state" operation. This figure shows that accurate process measurements cannot be made until the temperature profile no longer is changing over time, which even in a small sample can take a very long time to be established.

[9] Birrell, Heat Transfer Ahead of a SAGD Steam Chamber: A Study of Thermocouple Data From Phase B of the Underground Test Facility (Dover Project), Journal of Canadian Petroleum Technology, March 2003

At quasi-steady state conditions, the bitumen interface moves with a constant velocity and the solvent condenses at a constant rate determined by the temperature gradient (i.e. conduction heat loss) at the bitumen interface. If we consider the temperature gradient at the bitumen interface, (i.e. slope of the temperature profile at x=0), then FIG. 1 shows that temperature gradient is far too high, and consequently the solvent condensation rate will be substantially in error for the first seven days of an experiment.

In addition to the problem of achieving quasi-steady state temperature profiles, the parasitic heat losses can be 10-100 times larger than the expected heat delivery rate. If solvent condensation is the only source of heat in the experiment, then these parasitic heat losses result in solvent condensation rates 10-100 times too high. High solvent condensation rates are undesirable and can lead to a host of complications including flooding of the vapour chamber with liquid and destabilization of asphaltenes. Thus, it is important to minimize the parasitic heat losses and correctly approximate the quasi steady-state temperature profiles for an accurate simulation to occur.

Thus, in the absence of appropriate scaling assumptions, which shorten the time of the physical experiments, real time experiments are required. In real time experiments, temperature effects become of much greater concern and represent significant limitations on experimental accuracy. What is needed is an experimental technique and apparatus in which the parasitic heat losses and temperature profiles are controlled in a way that permits measurements to be made which accurately reflect insitu circumstances, without an undue amount of time being required. The data generated by such techniques can then be used to develop accurate empirical models.

BRIEF SUMMARY OF THE INVENTION

The present invention teaches method and apparatus for testing solvent extraction processes for the tar sands. Such testing is desirable to determine the impact of changes in process conditions on the bitumen yield, extraction rate and the degree of upgrading for among other things, heated solvent processes. An object of the present invention is to permit real time testing to occur, without needing to run each experiment for many days before experimental sampling can even begin.

What is desired is a means to configure temperature profiles within testing samples to simulate predetermined insitu temperature profiles. In this respect predetermined temperature profiles can be selected to, for example, minimize parasitic heat losses and to also minimize the amount of time required to establish the preferred temperature profiles. Thus an object of the present invention is to permit relatively quick and accurate measurements to be made of solvent extraction processes.

An aspect of the present invention is to provide a method and apparatus that establishes temperature boundary conditions for an experimental sample undergoing a proposed extraction process, which properly mimic an insitu section of the reservoir. Thus, rather than using a scaling assumption to overcome such temperature sensitivities as in the prior art, the present invention provides a method of configuring a temperature profile of a sample being tested to simulate its insitu properties.

In one preferred embodiment the present invention provides a heat configurable sample holder, for holding the samples during the course of the experiment. The sample holder may, for example, be provided with an outer shell that incorporates individually controllable and localized heaters, each of which has thermal contact through the sample holder with the sample. Each of the heaters can be in the form of an electrical resistor, which is periodically energized to supply heat and a temperature sensor to measure the heater temperature. Each heater is preferably mounted on a thermally conductive base, which may take the form of a small tile. Each tile has sufficient thermal mass that the temperature fluctuation through a duty cycle is appropriate for the accuracy and precision of the temperature sensor. The tiles have high thermal conductivity to individually achieve a uniform temperature, but most preferably are thermally insulated from any adjacent tiles so that temperature gradients along the sidewall of the sample holder can be maintained without excessive heat loss. Thus the present invention provides a heat configurable sample holder, in which the temperature profile can be set according to any predetermined pattern, where the resolution of the temperature pattern is determined by the size of the individual tiles or conductive heater bases.

The present invention also provides for an array of temperature sensors placed within the tar sand sample being tested which produce an output enabling the temperature profile of the sample to be accurately measured. The sensed temperature profile is then processed through a mapping algorithm to determine a smoothed temperature profile within the sand. This temperature profile is used to establish the desired temperature for each individual tile. Thus an object of the present invention is to provide a control system which supplies an appropriate amount of power to the individual heater elements to allow the sample holder temperature profile to match the local internal sample sand temperature profile and thereby minimize any parasitic heat losses.

Therefore, according to an aspect of the present invention there is provided a method of testing, in a lab, an insitu extraction process comprising the steps of:
  placing a sample to be tested in a sample holder having a configurable temperature profile;
  placing the sample holder in a pressure vessel;
  increasing the pressure in the pressure vessel to simulate an overburden pressure;
  configuring the temperature profile of said sample holder to match a desired temperature profile,
  passing a solvent into said sample, and
  measuring one or more parameters of said oil extraction process.

In another aspect the present invention provides for:
  configuring a temperature profile of said sample holder to match a measured internal temperature profile of a sample arising during the application of an extraction process to said sample.

According to yet another aspect there is provided a testing device to conduct oil extraction process experiments on a sample to be tested, said testing device comprising a temperature configurable sample holder to provide a desired temperature profile to said sample.

The concepts taught in this patent may also have application in enhancing recovery of both heavy oil and less viscous oils.

BRIEF DESCRIPTION OF THE DRAWINGS

Reference will now be made, by way of example only, to preferred embodiments of the invention as illustrated in the accompanying drawings and in which:

FIG. 2b shows a side view of the heater tile array of FIG. 2a;

DETAILED DESCRIPTION OF THE PREFERRED EMBODIMENTS

FIG. 1 is calculated from the prior art as described in the background and illustrates the problems that the present invention seeks to address. FIG. 1 shows transient (one dimensional) temperature profiles at different times for a section of tar sand initially at 8 C when one edge is suddenly heated to 50 C, for example by a condensing solvent process. FIG. 1 also shows a "quasi-steady state" temperature profile for a bitumen extraction process taking place in 8 C tar sand with the interface heated to 50 C and an extraction rate of 5 cm/day. A physical model experiment must reproduce the appropriate "quasi-steady state" temperature profile, to accurately model insitu processes and thus to generate meaningful process test data. It will be understood by those skilled in the art that FIG. 1 only shows one-dimensional temperature profiles rather than the full 2D temperature map for the sake of clarity.

At "quasi-steady state" the sample has attained a temperature profile that mimics an insitu profile. In FIG. 1 the temperature profile of the quasi steady state curve is of constant shape, and even if the process continues, the shape will not change. The origin represents a bitumen interface, where the solvent vapour is condensing, and in absolute terms this interface will be moving at an estimated speed corresponding to the rate of extraction. However, even as the interface moves through the sample (mimicking movement through the reservoir in an actual extraction) the shape of the temperature profile extending out from the interface remains the same. In this specification the term "quasi-steady state" identifies a sample condition that will permit process testing to begin with meaningful measurements of process parameters being possible. Process parameters means any measurable aspect of a process that helps in defining the value properties or efficacy of a process, such as extraction rate, bitumen quality or the like. The term sample shall mean an actual sample of an insitu oil bearing formation, or a made up sample which is provided with certain characteristics to mimic the insitu reservoir conditions, or any other configuration of materials which may be used to provide tests on the process of interest. Typically, a sample will comprise a graded sand which is water wetted and oil saturated in a known manner.

Figure 2A:
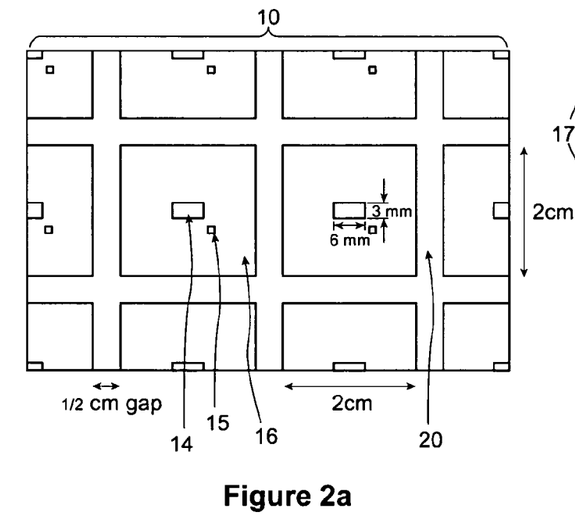
FIG. 2a shows a schematic of a section of the heater tile array for configuring temperatures according to the present invention.
Figure 2B:
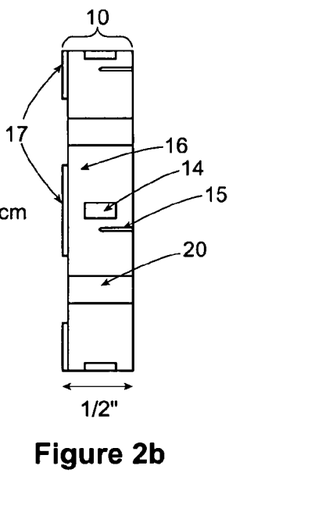

FIG. 2 shows a schematic of a section 10 of a temperature configurable sample holder according to the present invention. The section 10 shows a plurality of heater elements 14 embedded into heat conductive tiles 16. As shown the heating array may take the form of 2×2 cm tiles on a 2.5 cm pitch.

Each tile 16 is shown with an embedded resistor heater element 14 that is energized as needed to control the temperature of the tile 16. Although one heater per tile is shown, it will be understood that the present invention comprehends that more heaters may be added if needed to provide the desired amount of heat. However, one per tile is preferred. Each tile 16 is also equipped with a temperature sensor 15, which is preferred to be a type T calibrated thermocouple or the like.

The most preferred form of heater element 14 is a resistor heater element. A 100 ohm wirewound resistor provides adequate results. The type and properties of the heater can be varied, but what is needed is a heater power matched to a tile size to ensure that the local temperature within the apparatus can be matched by the tile temperature. For the purposes of the invention the resistor may be operated at power levels exceeding its' nominal rating. Destructive tests have shown that this is feasible, if the duration of the heating time is limited and the resistor is adequately thermally potted to limit temperature rise within the resistor. Consequently in the preferred form of the invention illustrated the resistor is placed within the tile and potted with a thermal conductive epoxy or the like such as Supertherm 2005 manufactured by Tra-Con Inc of Bedford Mass. Other configurations of heater element and tile combinations, such as surface mounted heaters that provide the advantages of a temperature configurable sample holder are also comprehended.

The tiles 16 are shown mounted in an insulating matrix 20, made from, for example, silicone rubber or the like. The tiles are separated by a gap of, for example, 5 mm which is large enough to reduce the heat transfer from one tile to the next but small enough to avoid excessive temperature drop (sag) between adjacent tiles. In some cases it is desirable to reduce the contact area of the tile 16 with the steel wall 32. Reduced contact area reduces the amount of conduction heat flux along the steel wall 32 without increasing the gap between the tiles. We can obtain the reduced contact area with a "knob" profile 17 at the contacting surface of the tile. The knob can be any convenient shape. Conventional wiring (not shown) connects the heater elements to an appropriate power source. Although any number of tiles may be used, it is estimated that 1024 tiles on a 2.5 cm pitch is sufficient to completely enclose a sample sandpack that is 32 cm high 62 cm long and 12 cm wide (i.e. 13×25×5 tiles). While it is preferred to make the array as regular as possible, various openings may be required in the array to accommodate thermocouple penetrations and whatever feed and drain ports that may be needed.

Figure 3:
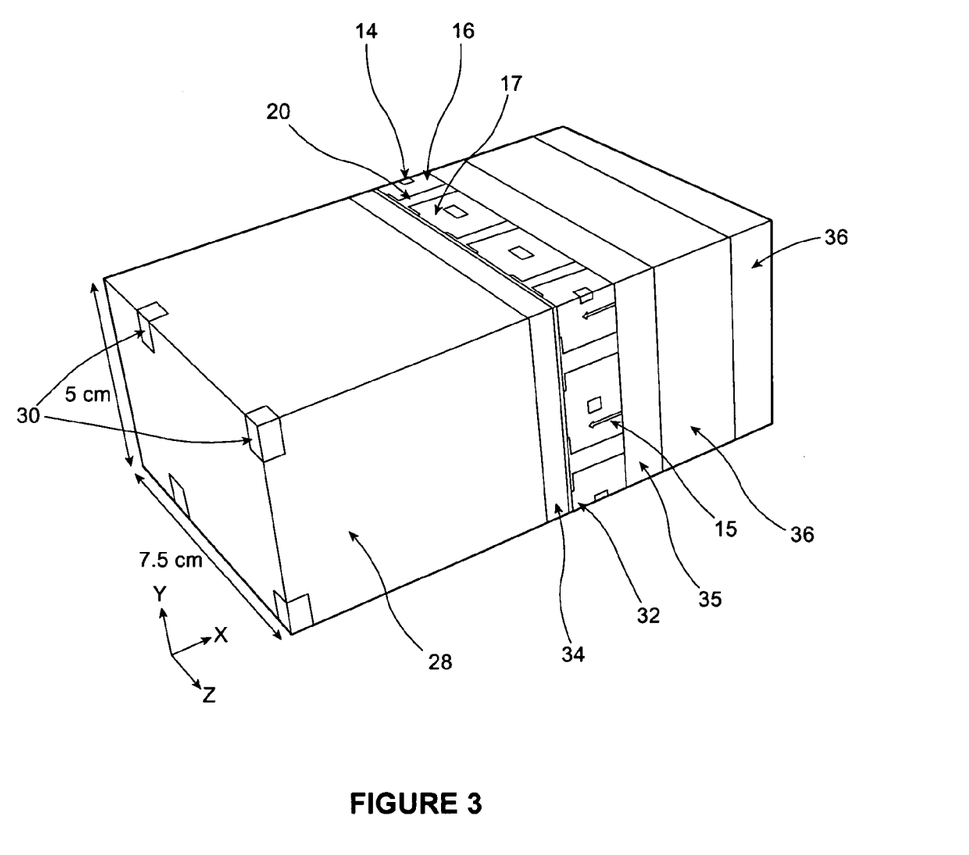
FIG. 3 shows a more detailed view of sample holder having a sample sandpack and the placement of insitu temperatures sensors according to the present invention.

FIG. 3 shows a more detailed isometric sectional view of the both the sandpack 28 and tile assembly. In FIG. 3, the sand pack 28 has temperature sensing thermocouples 30 which are preferentially placed on a uniform spacing (i.e. 5 cm spacing). Between the sand pack 28 and the wall of the sample holder 32 is a rubber liner 34 or the like to smooth the adjacent tile temperatures out so that the step profile of the tiles more nearly approximates the desired temperature profile of the sandpack 28. The liner 34 also helps to dampen out fluctuations arising from the power duty cycle. The layer of heater tiles is immediately outside the wall 32 and is physically clamped to the wall 32 to provide good thermal contact between the tile assembly and the wall. This thermal contact is important to ensure that each tile can determine the local temperature of the side wall 32 of the sample holder. Beyond the tiles are several external layers which include the packaging 35 (wiring and mounting for the tiles) as well as insulation 36 to reduce the heat delivery requirement of the tiles.

The tiles are preferably made of a high conductivity material such as aluminum or copper or the like, so they will individually maintain a fairly uniform temperature across an individual tile. The smooth temperature profile in the tar sand undergoing stimulation is thus approximated by a sample holder temperature profile having a number of steps, each step representing a different tile. It will be understood by those skilled in the art that the quality of the approximation depends on the resolution (i.e. tile size). Therefore the more numerous and smaller the individual tiles, the more exactly the temperature profile to the sand pack 28 can be matched. A reasonable match is required to ensure reasonably accurate experimental results. Furthermore, the individual tiles may or may not be continuously energized so that their temperature may fluctuate slightly through a duty cycle. Providing liner 34, which has some thermal resistance, mitigates these sources of error. By placing it on the inside of the sample holder it will act to dampen out the duty cycle temperature fluctuations and also smooth out the tile temperatures across the assembly.

It can now be appreciated that during any experimental run the temperature of each tile can be set to any desired temperature. This has two important advantages. Firstly, the desired insitu temperature gradients can be externally imposed on the tar sand sample before the solvent is introduced or the process experiment otherwise begun. Then, when the actual process testing is started, for example by injecting the solvent into the sample tar sand pack, the individual tile setpoints can be determined by mapping the internal temperatures within the tar sand as described below. This strategy allows the experiment to start close to the desired "quasi-steady state" temperature profile and thereby minimize the duration of the thermal transient period. This strategy provides a substantial time/cost savings and greatly improves the usefulness of the data since realistic solvent/oil ratios can be obtained right from the beginning of the experiment.

In addition, once the process has begun, and heat is being supplied to the sample by means of the process being tested, appropriate thermal boundary conditions can be provided by the temperature configurable sample holder of the present invention. It is preferred to use the temperature measured at the closest adjacent thermocouples 30 within the sand pack 28 as the basis for calculating the tile setpoint temperature. Temperature profiles in a heated gravity drainage process have been previously measured (Birrell[9]) and according to the present invention insitu temperature profiles can be readily interpolated or extrapolated from an array of temperature sensors in the sample. Interpolation and/or extrapolation of these curves together with the location of the individual tile determine the desired temperature for a particular tile.

This mapping is most convenient if the thermocouple spacing within the tar sand pack is a simple multiple of the tile spacing. For example, with 5 cm spacing on the thermocouples it is most convenient to have tiles on a 2.5 cm pitch.

Figure 4:
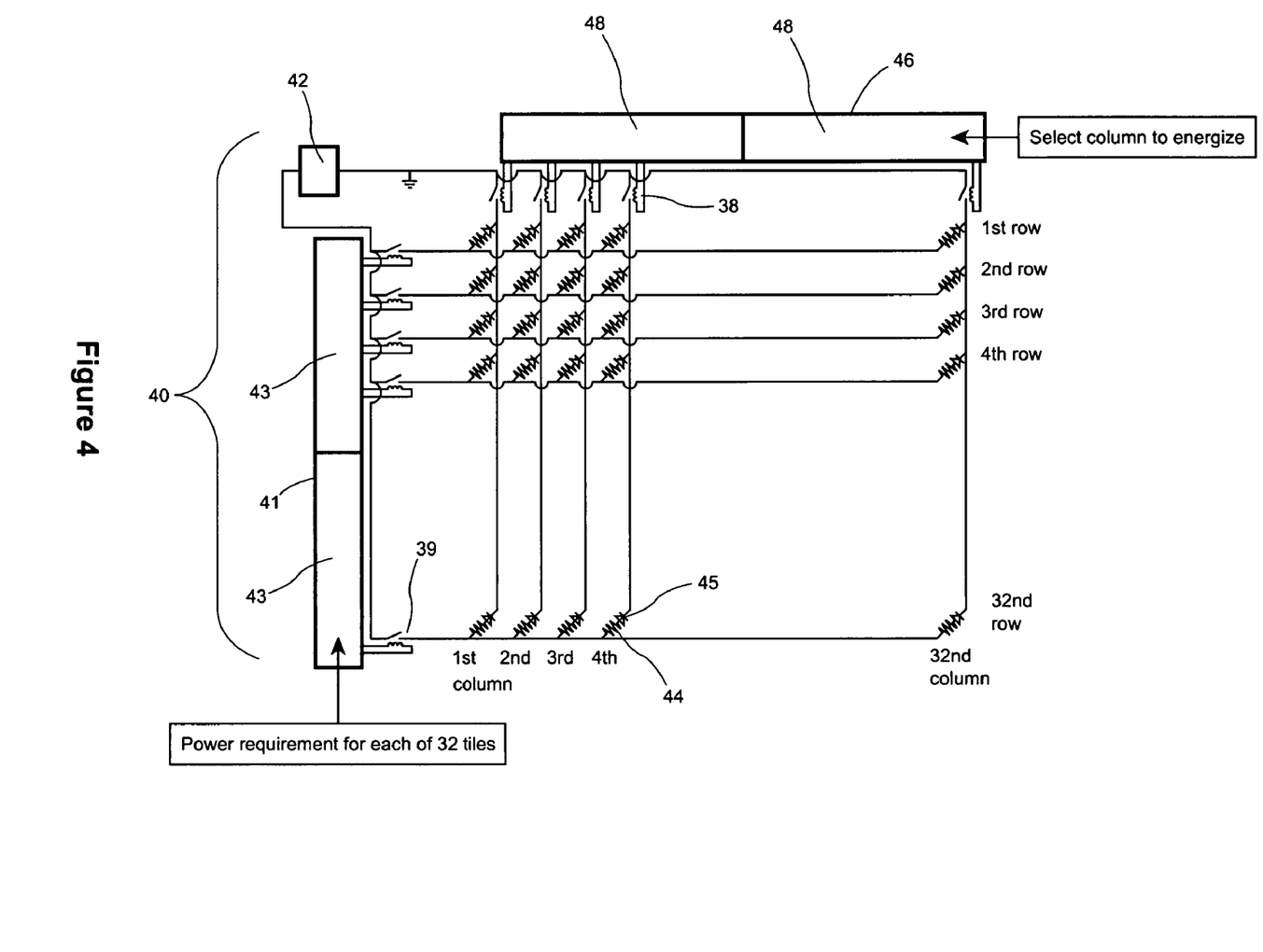
FIG. 4 shows a schematic of a power circuit to energize individual tiles according to the present invention.

FIG. 4 shows a power circuit 40 to energize the individual tiles. In a preferred embodiment the power is delivered by a 24 volt 8 Amp DC Power Supply 42. The power is dissipated in a 100 ohm resistor 44. Thus, each tile is energized with approximately 6 watts of power. As each tile includes a temperature sensor, the control system will apply power according to a difference between the desired tile temperature and the actual tile temperature. The size of the difference will determine the length of time that the power is applied to any individual tiles. An adequate configuration is for a ground connection multiplexer or "drain multiplexer" 46 to cycle through each of the 32 columns in the preferred tile array with a 1 second dwell time for each tile column in the array.

An example arrangement for the drain multiplexer 46 is to use two digital switch banks 48. Adequate results can be obtained from National Instrument Field Point Digital Switch Banks (each having 16 software programmable switches) part number FP-DO-401 to drive individual 8 amp rated relays 38. For such a mechanical relay arrangement, it is preferential that all 32-power controller switches 39 are open circuit (i.e. there is no current flow) during the short time interval when the drain multiplexer switches from one column to the next.

Thus, in this configuration a particular tile will cool continuously during 31 seconds of the cycle and will be energized during the final second of the 32-second cycle in order to achieve its target temperature. The maximum power output of this particular configuration is about 180 watts. Other configurations and cycle times are comprehended by the present invention, but the foregoing yields satisfactory results.

The output power controller 41 regulates power delivery to each of 32 individual tiles by controlling a length of time that each tile is energized by the DC supply. Again two Field Point Digital Switch Banks 43, can be used to actuate a total of 32 power control relays 39. For example, if 3 joules of energy are required for a particular tile then the tile would only be energized for 0.5 seconds. The combination of power controller, drain multiplexer and the individual diodes 45 associated with each power resistor avoids the problem of parallel current paths thereby ensuring that the correct tiles is addressed and individually energized at the appropriate level. This arrangement is particularly convenient, because it allows a common wire to energize all the tiles in a particular row and a common drain wire to return current to ground for a particular column. The arrangement described can uniquely address and deliver power to 1024 individual tiles (i.e. =32 columns×32 rows).

A large cost is associated with providing individual power supplies and controllers for each heater tile. The preferred configuration uses one power supply and an appropriate arrangement involving digital switches and diodes to individually and uniquely address a large number of tiles. The present invention therefore comprehends using the same to uniquely address and energize individual tiles in a matrix consisting of 1024 tiles via 32 individual power switches 39, a resistor 44 and diode 45 pair on each tile, and one 32 channel drain multiplexer 48 which connects to ground.

With experiments conducted in pressure vessels, there is always a safety/reliability concern with electrical feedthroughs through the wall of a pressure vessel. Although feedthroughs are well known and commonly used, they represent a possible leak path and present a risk of catastrophic failure. Thus, it is desirable to minimize the use of pressure wall electrical feedthroughs. For example, with 1024 tiles there would typically be 2048 thermocouple wires that would have to pass through the wall of the pressure vessel. However, the preferred configuration of the present invention is to place most of the electronics (multiplexers, digital switches, relays, data acquision cards, power supplies, plc's etc) within the pressure vessel so they operate at elevated pressure and then to communicate to an external computer via a single high-speed connection like an Ethernet link. This is outside the nominal operating specifications of some components but pressure tests have demonstrated that reliable operation can be achieved. This simplifies the design and greatly increases mechanical reliability. The present invention also comprehends using wireless, optical or other signal communication that does not require a penetration through the wall of pressure vessel.

Figure 5:
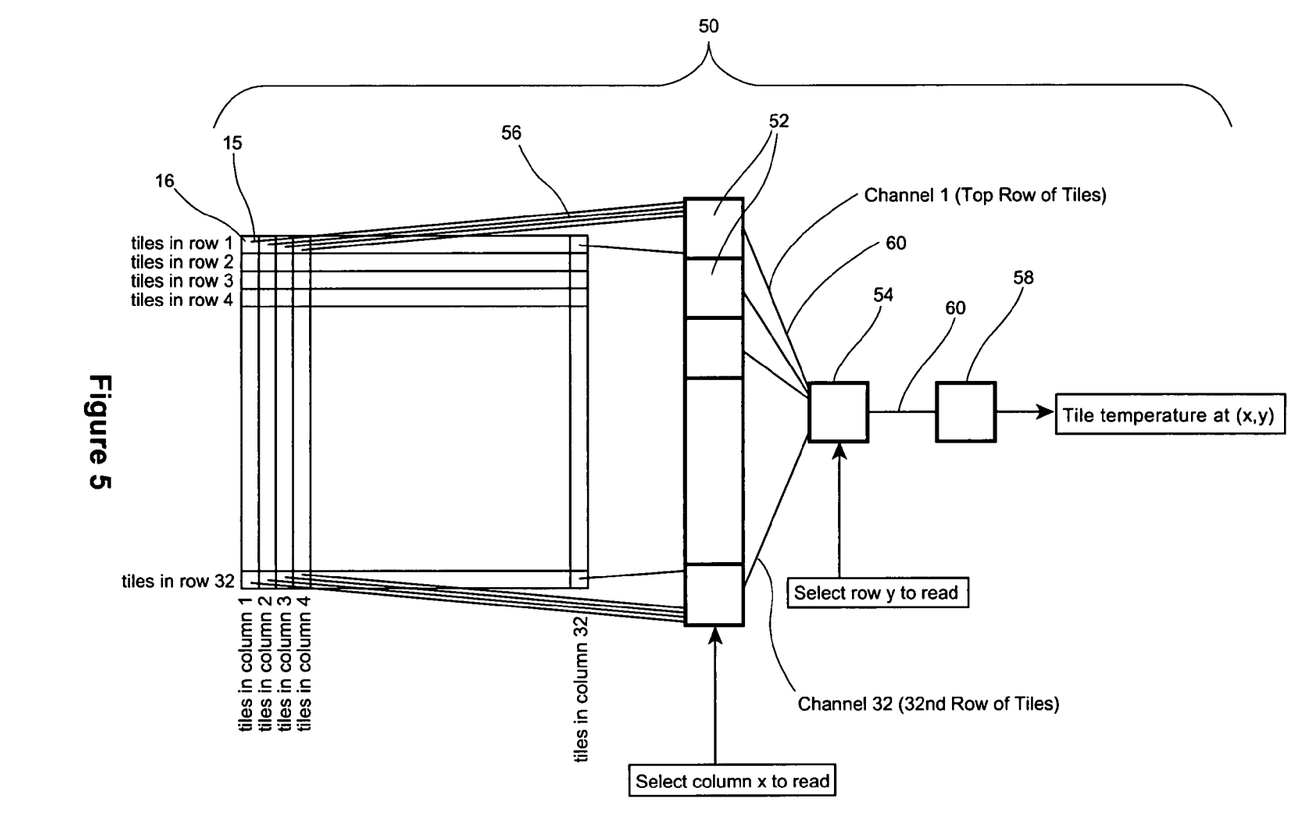
FIG. 5 shows a schematic of a data acquisition system and the means whereby a particular heater element interacts with the data acquisition system.

FIG. 5 shows a schematic of a data acquisition system 50 to address and measure a temperature of each individual tile 16. As previously noted, each tile has an individual temperature sensor 15. Preferentially the sensors 15 are type T thermocouples or the like that have sufficient sensitivity and accuracy. The sensors will be calibrated insitu With the appropriate wiring in a known manner. Each thermocouple is connected to an input multiplexer 52. Each row of tiles is connected to a common multiplexer 52. Input from the control system controls the switching of the multiplexers 52 to selective read temperatures in a particular column of tiles. Further input from the control system controls the switching of the multiplexers 54 to select the appropriate row of tiles for measurement by the data acquisition system 58. In this way, the data acquisition system can address each tile individually. Unfortunately, there is no easy arrangement to share common wires, so 2048 individual wires 56 are required to measure the temperatures of 1024 tiles. For clarity, in FIG. 5, each single line 56 actually represents two thermocouple leads. The multiplexers 52, 54 are ADG732 from Analog Devices and are mounted on small printed circuit boards (PCB) in order to provide a good mechanical for support for the wire terminations.

Similar to the energizing of the heater tiles, a large cost is potentially associated with providing individual data acquisition channels for each thermocouple. The present invention provides an efficient configuration since the thermocouples for each tile (i.e. 1024 thermocouples) are connected through a series of multiplexers to a 32-channel data acquisition system. These multiplexers provide a means to uniquely address each individual thermocouple as explained above.

Cold junction error could be introduced into the thermocouple readings by the wire connections. To minimize this type of error it is desirable to make the PCBs small and place them in a well-ventilated location so the PCB's are effectively isothermal, thereby canceling out any cold junction errors. Furthermore, it is important to use the appropriate thermocouple lead wire 60 for all subsequent connections back to the data acquisition system Again for clarity, each thermocouple lead wire 60 actually represents two thermocouple leads.

Figure 6:
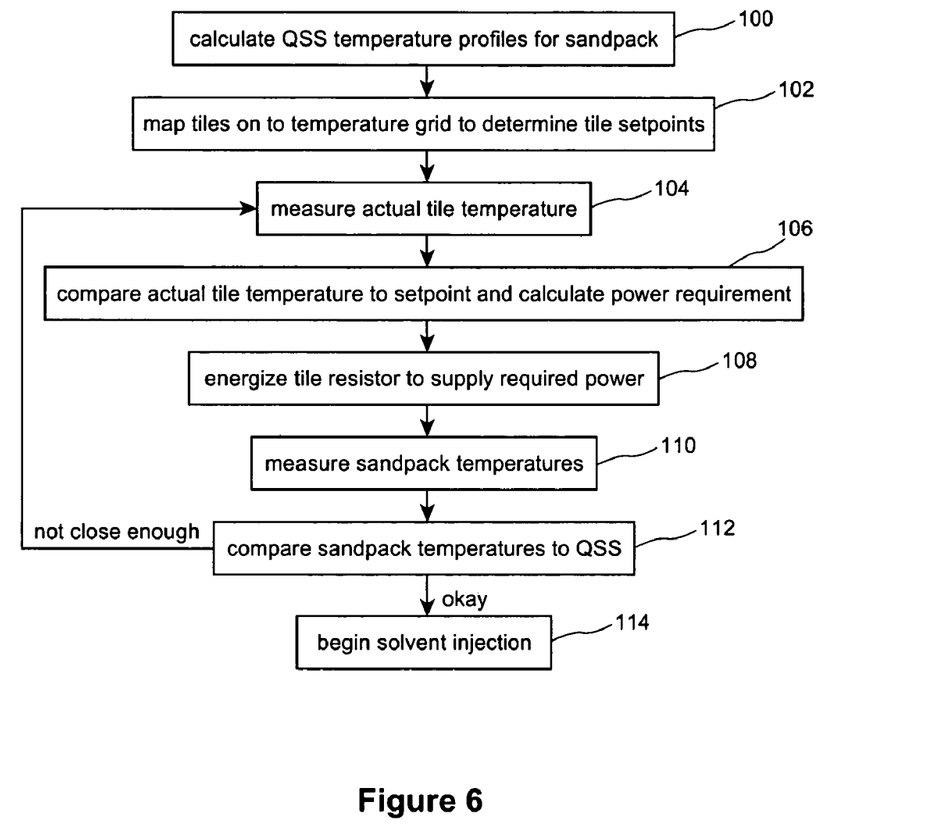
FIG. 6 outlines the temperature control algorithm during startup for the present invention.

FIG. 6 depicts a startup temperature control algorithm. Good results have been obtained from software coded in National instruments Labview programming language downloaded into a National Instruments Field Point controller At start up, the present invention is able to configure a desired temperature profile in the sample holder at a given expected (either calculated or estimated) Quasi-Steady State (QSS) temperature profile. Being able to directly apply this temperature profile to configure the profile of the sample sandpack greatly reduces the length of time taken to get to this condition.

According to the present invention an estimate is made of the bitumen interface velocity in order to calculate the QSS. However, this may well be one of the parameters being determined by the experiment. Where the extraction rate is not known beforehand (an arbitrarily assumption of 5 cm/day was used in FIG. 1), an estimate for the QSS can be made and as the experiment proceeds the actual bitumen interface velocity is determined. The length of any transient period between start up and achieving QSS will depend on the accuracy of the first estimate.

Thus, FIG. 6 shows the following steps. At 100, determine the expected QSS profile. At 102, map the individual tiles onto the QSS grid to determine the desired temperatures for the tiles. At 104, measure the actual tile temperature and then calculate the appropriate amount of power that should be delivered to the tile to reach the desired temperature. At 106, energize the heater on the tile to deliver the appropriate amount of power. At 108 the sandpack temperature is measured. At 110 the sandpack temperature is compared to the desired temperature. At 112 the cycle is continued until the tile temperature and the sandpack temperatures match the QSS target. This may take between 4 and 24 hours depending on the size of the sandpack and the exterior insulation. When the QSS profile is achieved then the process experimentation can proceed and, for example, solvent can be introduced into the sandpack 114.

According to the present invention the 2D slice of the reservoir that the experiment simulates should have no heat loss through the sidewalls, so the two sidewalls should be perfectly adiabatic. Thus, in addition to reducing the time to achieve QSS, the present invention eliminates parasitic heat losses which otherwise can distort the experimental results. Eliminating parasitic heat losses does not mean perfect insulation. To properly mimic the insitu conditions also requires a controlled amount of heat loss or flux, through the top, bottom and end walls of the sample holder to represent the temperature gradients and heat fluxes that would extend beyond the can into the surrounding "virtual" tar sand matrix. For example if we refer to FIG. 1 it shows, for a quasi steady-state profile, a temperature gradient occurs at 0.6 m (i.e. the end of the can). Controlled heat loss at the top bottom and end of the can is provided by accounting for the insulating quality of the liner and then calculating the appropriate temperatures for individual tiles to match the heat fluxes necessary to simulate the external temperature gradients. For example, since the thermal conductivity of silicone rubber is about 10% of that of typical tar sand, a rubber liner thickness inside the can of 2.5 mm has the same heat loss characteristics as a tar sand layer having a thickness of 2.5 cm. This provides a simple and convenient way to calculate the appropriate desired tile temperatures at the top, bottom and end of the can needed to match the heat flux boundary conditions. Using the equivalent "tar sand" distance of the rubber liner extrapolating from a smoothed sandpack temperature grid the appropriate desired tile temperatures can be found for the top, bottom and end walls.

Figure 7:
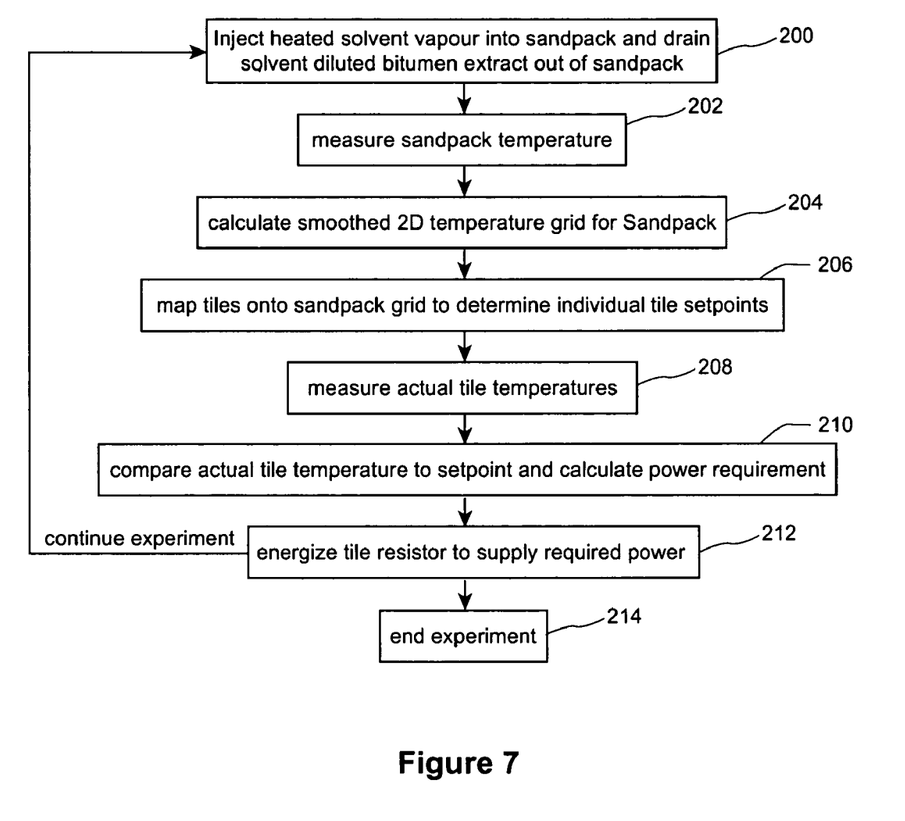
FIG. 7 outlines a tile temperature control algorithm during operation after the solvent vapour is injected into the sample sandpack.

FIG. 7 shows the temperature control algorithm while in the midst of conducting an actual process trial. Heated solvent vapour is being injected into the sandpack causing solvent diluted bitumen to drain from the sandpack. During this process the tile setpoint temperatures are determined by the measured internal temperatures within the sandpack instead of the estimated QSS temperature grid. FIG. 7 shows that the control system algorithm cycles through the following steps. At 200, measure sandpack temperature, at 202 calculate smoothed 2D temperature grid for the sandpack. At 204 map the tiles onto the sandpack temperature grid to determine the setpoint temperature for individual tiles. At 206 measure the actual tile temperature and calculate the appropriate control action. And finally, at 208 energize the tile to supply the required amount of heat.

For the 32×32 heater tile matrix described above, the individual heater tiles are energized for one second out of 32. The temperature drop during the 31 seconds of cooling is determined by the heat loss (i.e. conduction heat loss along the side of the can, insulation+exterior temperature and by the thermal inertia of the tile). The magnitude of any temperature "bounce" can be reduced by increasing the heat capacity of the tile (i.e. the tile thickness), increasing the external temperature, or increasing the insulation. Referring to FIG. 1, we can see that for an experiment at 50 C the QSS indicates that the lowest temperature is about 33 C at 60 cm from the interface. Thus a minimum exterior temperature of about 25 C is likely required (to allow 33 C with heat conduction taking place along the side walls). With a reasonable amount of insulation the cooling rate of a tile at 50 C is 0.01 C/second, so the tile temperature will drop about 0.3 C in a 30 second cycle.

To obtain the most accurate tile temperature measurement for control, it is preferred to measure its temperature just prior to applying power (i.e. at 31 seconds into the cycle in the example). With this configuration the tile temperature typically is within 0.2 C of the target setpoint temperature.

Figure 8:
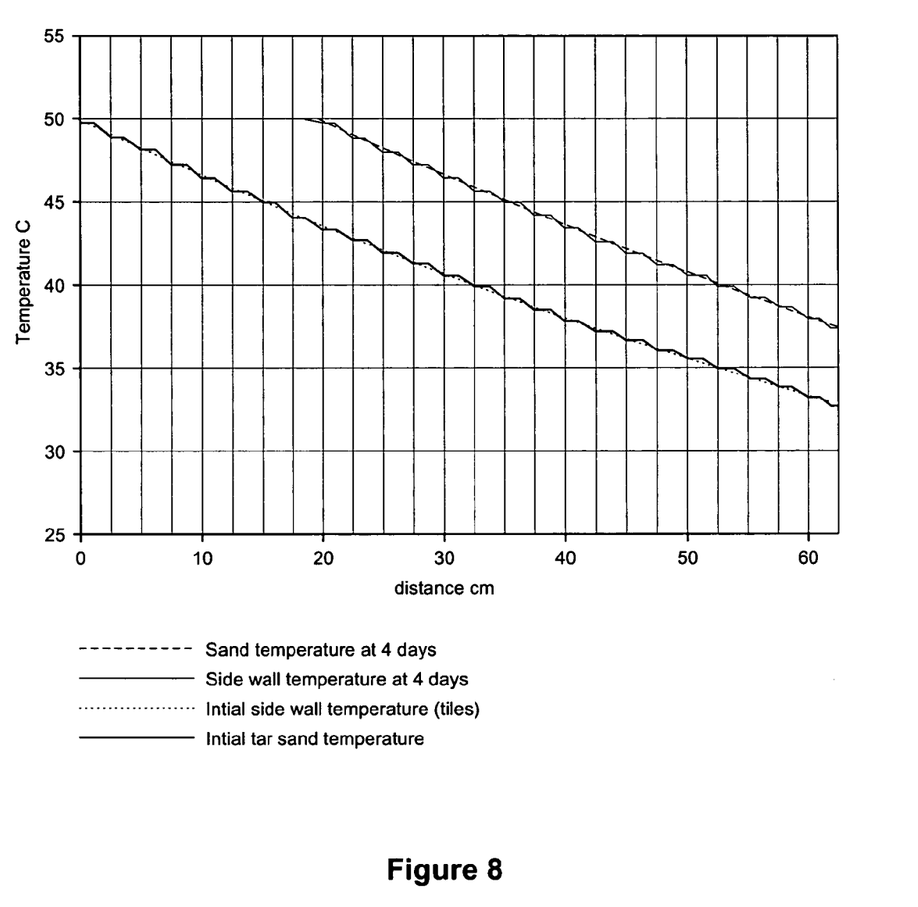
FIG. 8 compares the target "quasi-steady state" temperature profiles within a sample sandpack to predicted temperature profiles along a side wall of a sample holder of the present invention. Temperature profiles are shown at startup and again after 4 days, assuming an interface velocity of 5 cm/day.

FIG. 8 compares the expected temperature profiles within the tar sand (i.e. QSS profiles) to the temperature profiles achieved along the side wall by the present invention. Profiles are shown at startup and again at 4 days into an experiment assuming an interface velocity of 5 cm/day. The tiles match the temperature profile but also introduce a temperature error due to the step changes in temperature between adjacent tiles. FIG. 8 shows that the maximum temperature error (i.e. the difference between the tar sand and the wall temperature) is about 0.3 C. For a rubber liner of ¼", this is equivalent to a parasitic heat loss near the bitumen interface less than 1% of the target heat delivery rate. Including a ±0.2 C "bounce" from the duty cycle of the control system, the total heat loss error should be within a few percent of the ideal (i.e. insitu reservoir) case. By comparison a highly insulated configuration which is not configurable as is the present invention will still have parasitic heat losses 10 to 100 times larger than the total target heat delivery rate, making experimental results all but meaningless.

It can now be understood how the present invention may be used to determine a true bitumen extraction rate. There are several criteria that can be used. First, the location of any vapour chamber that forms can be measured by means of the sandpack thermocouples. The temperature profile will indicate a position of the bitumen interface. By tracking its position over time an extraction rate can be determined. A solvent delivery rate (i.e. condensation rate) can also be measured and used to determine if the heat delivery rate is consistent with the displacement of the bitumen interface. (i.e. does the heat balance close?). Closing the heat balance verifies that a true measurement was made that is not distorted by temperature transients. We can estimate bitumen yield (i.e. the rate of bitumen recovery) by comparing actual bitumen production (i.e. after removing the solvent) to the interface position. All of these may be referred to as parameters of the extraction process. The foregoing is not intended to be restrictive and it will be realized that other parameters can also be measured to help analyze the efficacy of various production techniques.

It will be appreciated by those skilled in the art that while the foregoing description relates to preferred embodiments of the invention various alterations and modifications are possible without departing from the broad scope of the appended claims. For example, while the foregoing discussions are centered on a condensing solvent extraction process, the present method and apparatus could be used on other types of thermally based insitu recovery processes, such as being used to study bitumen extraction in SAGD type processes. The components (i.e. power resistors, wiring etc) would have to be appropriately sized to operate higher temperatures which are typical of such SAGD processes. In addition there also are processes that propose to use solvents mixed into the steam that would be good candidates for using the present invention, since the prior art scaling criteria for any solvent processes is in doubt.

We claim:

1. A device to test oil extraction processes on a sample representative of an in situ oil bearing formation, said device comprising a temperature configurable sample holder having sufficient temperature control to provide a desired temperature profile to said sample holder to match temperature conditions arising in said sample from said oil extraction process being tested and a sample representative of an in situ oil bearing formation located within the sample holder and subjected to the temperature profile.

2. A device to test oil extraction processes on a sample as claimed in claim 1 further including a resistance electrical heater means for configuring said temperature profile.

3. A device to test oil extraction processes on a test sample as claimed in claim 2 wherein said heater means includes a plurality of individual resistance heaters and a power supply.

4. A device to test oil extraction processes on a test sample as claimed in claim 3 wherein each heater is associated with a heat conductive heating tile.

5. A device to test oil extraction processes on a test sample as claimed in claim 4 wherein each tile further includes a temperature sensor to sense a temperature of said tile.

6. A device to test oil extraction processes on a test sample as claimed in claim 5 wherein each tile is of sufficient size to remove enough heat from said heater to avoid thermal failure off said heater at normal operating conditions.

7. A device to test oil extraction processes on a test sample as claimed in claim 6 wherein each tile has sufficient thermal inertia to avoid a significant temperature bounce between energizations.

8. A device to test oil extraction processes on a test sample as claimed in claim 3 wherein said power supply can independently energize each of said heaters.

9. A device to test oil extraction processes on a test sample as claimed in claim 4 wherein an insulator is provided between each tile to prevent the temperature of one tile from unduly affect the temperature of an adjacent tile.

10. A device to test oil extraction processes on a test sample as claimed in claim 4 where said heating tiles are sized and shaped to smooth said temperature profile of said sample holder.

11. A device to test oil extraction processes on a test sample as claimed in claim 4 wherein each tile has a reduced contact area for transmitting heat to said sample.

12. A device to test oil extraction processes as claimed in claim 4 wherein adjacent tiles are separated by an insulated space to reduce heat conduction along a length of said sample.

13. A device as claimed in claim 4 wherein diode and drain multiplexers are used to provide for individual control of each heating tile without requiring separate power controls for each tile.

14. A device to test oil extraction processes on a test sample as claimed in claim 1 further including a control system to permit said temperature profile to be controlled according to desired temperature configurations.

15. A device to test oil extraction processes on a test sample as claimed in claim 14 further including a plurality of individual resistance heaters and a power supply, wherein said control system uses thermal inputs of temperature sensors in said sample to configure said temperature profile of said sample holder by selective energizations of said resistance heaters.

16. A device to test oil extraction processes as claimed in claim 1 further comprising a plurality of temperature sensors at spaced apart locations within said sample to measure a temperature at said locations in said sample.

17. A device to test oil extraction processes on a test sample representative of an in situ oil bearing formation, said device comprising:
　　containing a sample representative of an in situ oil bearing formation profile
　　an array of heating tiles located in proximity to the sample holder to permit said sample holder and said sample to achieve a desired temperature profile, to match a temperature profile generated within said sample by said extraction process being tested;
　　an electrical insulator between each of said heating tiles and between said heating tiles and said sample holder, a layer of insulation around said array of heating tiles; and a source of power sufficient to energize said heating tiles to achieve said desired temperature profile.

* * * * *